(12) United States Patent
Okumura et al.

(10) Patent No.: US 6,828,378 B2
(45) Date of Patent: Dec. 7, 2004

(54) COMPOUND COMPRISING CROSSLINKED POLYROTAXANE

(75) Inventors: Yasushi Okumura, Tsukuba (JP); Kohzo Ito, Tokyo (JP)

(73) Assignee: Center for Advanced Science and Technology Incubation, Ltd., Tokyo (JP)

(*) Notice: Subject to any disclaimer, the term of this patent is extended or adjusted under 35 U.S.C. 154(b) by 0 days.

(21) Appl. No.: 10/258,642

(22) PCT Filed: Apr. 27, 2001

(86) PCT No.: PCT/JP01/03717

§ 371 (c)(1),
(2), (4) Date: Oct. 25, 2002

(87) PCT Pub. No.: WO01/83566

PCT Pub. Date: Nov. 8, 2001

(65) Prior Publication Data

US 2003/0138398 A1 Jul. 24, 2003

(30) Foreign Application Priority Data

Apr. 28, 2000 (JP) .................................... 2000-129467

(51) Int. Cl.[7] .................. C08B 37/16; A61L 27/18; A61L 15/26; A61F 2/10; A61F 2/14
(52) U.S. Cl. .................. 525/55; 525/403; 525/418; 525/420; 525/452; 525/454; 525/461; 525/919
(58) Field of Search .................. 525/55, 919, 403, 525/418, 420, 452, 454, 461

(56) References Cited

U.S. PATENT DOCUMENTS 6,037,387 A    3/2000   Yui et al.
6,100,329 A  * 8/2000   Gibson et al. ............. 525/55

FOREIGN PATENT DOCUMENTS

EP    1 316 324 A1  *  4/2003
JP    06/025307        2/1994
JP    07/048451        2/1995

OTHER PUBLICATIONS

Gong et al, "Self–Threading–Based Approach for Branched and/or Cross–linked Poly(methacrylate rotaxane)s", 1997, J. Am. Chem. Soc., 119(25), 5862–5866.*

Gong et al, "Controlling Polymeric Topology by Polymerization Conditions: Mechanically Linked Network and Branched Poly(urethane rotaxane)s with Controllable Polydispersity", 1997, J. Am. Chem. Soc., 119(37), 8585–8591.*

Oike et al, "A Cyclic Macromonomer Designed for a Novel Polymer Network Architecture Having Both Covalent and Physical Linkages", 2001, Macromolecules, 34(18), 6229–6234.*

Ichi, Takahiro, et al., "Preparation and Characterization of Three–Dimensional Architecture Based on Polyrotaxane Structure", The 12th Bioengineering Conference 1999 Annual Meeting of BE D/JSME.

Imakita, S., et al., "Synthesis and Characterization of polyrotaxane–Crosslinked Hydrogels", Polymer Preprints, Japan, 46:3 (1997), pp. 360.

Gong, Caiguo, et al., "Self–Threading–Based Approach for Branched and/or Cross–linked Poly(methacrylate rotaxane)s", J. Am. Chem. Soc. 1997, 199:25, 5862–5866.

* cited by examiner

Primary Examiner—Nathan M. Nutter
(74) Attorney, Agent, or Firm—Morgan & Finnegan, LLP

(57) ABSTRACT

A novel compound and novel gelatinous substance which have high absorbability, uniform expansion, and elasticity. Although conventional gels include chemical gels and physical gels, no novel gels or compounds have been realized which have fracture resistance, high entropic elasticity, and biodegradability. The present invention provides a novel compound and a novel gelatinous substance which each comprises a crosslinked polyrotaxane obtained by chemically bonding two or more polyrotaxane molecules through the cyclic molecules or rotators thereof.

73 Claims, 3 Drawing Sheets

COMPOUND COMPRISING CROSSLINKED POLYROTAXANE

FIELD OF THE INVENTION

The present invention relates to a novel compound and a novel gelatinous material having high absorbability, uniform expandability, and elasticity or viscoelasticity. In particular, the present invention relates to a compound comprising crosslinked polyrotaxane, which is obtained by linking two or more polyrotaxane molecules through chemical bonds between cyclic molecules or rotators in the inter-polyrotaxane-molecules.

DESCRIPTION OF THE PRIOR ART

To date, there are various chemical and physical gels. Among these gels, chemical gels in general have a so-called network structure in which macromolecules are crosslinked to each other. Such a network structure has some problems: when tension is applied to chemical gels, the structure is broken down at locations where the distances between the crosslinking points are short, whereby the gel undergoes non-uniform destruction, since the structure does not have uniform distances from a crosslinking point to its neighboring points. On the other hand, physical gels are subjected to gelation by the attraction force between polymers. However, physical gels have problems: physical gels melt or dissolve at high temperatures or in solvents, and crystallize at low temperatures, since their structures are formed by the attraction force and the physical gels tend to undergo permanent deformation.

Gels in which crosslinking points are movable, gels in which multiple polymeric molecules are slidable against each other, the so-called slipping or sliding gels, have been proposed as models since 1950s in well known studies. The possibilities for a variety of applications of such gels have been discussed. However, such gels have not been actually made, and researchers have been focused on how to produce such gels.

Japanese Patent Laid-open Publication (JP-A) No. 6-25307 discloses compounds referred to as so-called polyrotaxane. These compounds are molecules in which plural alpha-cyclodextrin molecules as a rotator and a polyethylene glycol molecule as the axis are assembled by means of non-covalent bonding and each end of the axis is blocked with a blocking group. That is, compounds are disclosed in which a polyethylene glycol molecule has alpha-cyclodextrin molecules included in a skewered manner and each end of the polyethylene glycol molecule is blocked with a blocking group so as not to allow eliminating the alpha-cyclodextrin molecules from the polyethylene glycol molecule.

Although there are various chemical gels well known to date, all of these gels are characterized by their gradual breakdown against tension or stress. In other words, chemical gels undergo deformation in response to stress. Even though the shape of a chemical gel is retained as a whole, portions of the gel undergo microscopicaldestruction. Thus, chemical gels suffer from gradual breakdown. On the other hand, physical gels always tending to undergo permanent deformation leading to melt down at high temperatures, dissolution in solvents, and crystallization at low temperatures.

In addition, so-called slipping or sliding gels have been discussed in theory, and not realized yet.

Furthermore, JP-A No. 6-25307 discloses polyrotaxane that is a novel compound, and a process for producing the same, but does not describe its uses.

SUMMARY OF THE INVENTION

An object of the present invention is to provide a third gel, that is, a novel gel having a structure and properties which are not possessed by conventional chemical and physical gels.

Further, an object of the present invention, as another object or in addition to the above-described object, is to provide a novel gel or compound in which movable crosslinking segments allow stress to be dispersed within the gel or compound, thereby providing the gel or compound with a higher fracture strength than those of chemical gels.

More, as another object or in addition to the above-described objects, an object of the present invention is to provide a novel gel or compound having higher entropic elasticity than those of physical gels.

Moreover, as another object or in addition to the above-described objects, an object of the present invention is to provide a novel biodegradable gel, a novel biodegradable compound that can be readily degraded by microorganisms.

The inventors have carried out intensive research, and as a result, found that the objects described above can be achieved by the present invention as illustrated by the following <1> to <77>:

<1> A compound comprising crosslinked polyrotaxane, wherein the crosslinked polyrotaxane has a first and a second polyrotaxane, the first polyrotaxane having a first linear molecule and a first cyclic molecule, the first linear molecule having the first cyclic molecule included in a skewered manner which allows the first linear molecule to pass through the opening of the first cyclic molecule, and having at each end a first blocking group which is placed so as to prevent the elimination of the first cyclic molecule; and the second polyrotaxane having a second linear molecule and a second cyclic molecule, the second linear molecule having the second cyclic molecule included in a skewered manner which allows the second linear molecule to pass through the opening of the second cyclic molecule, and having at each end a second blocking group which is placed so as to prevent the elimination of the second cyclic molecules, each opening of the first and second cyclic molecules is of substantial ring, and the crosslinked polyrotaxane is formed by linking at least one of the first cyclic molecules and at least one of the second cyclic molecules via chemical bonding.

<2> In the compound of item <1>, the first blocking group may have bulkiness and/or ionic property, thereby preventing the elimination of the first cyclic molecules.

<3> In the compound of item <1> or <2>, the second blocking group may have bulkiness and/or ionic property, thereby preventing the elimination of the second cyclic molecules.

<4> A compound comprising crosslinked polyrotaxane, wherein the crosslinked polyrotaxane has a first and a second polyrotaxane, the first polyrotaxane having a first linear molecule and a first cyclic molecule, the first linear molecule having the first cyclic molecule included in a skewered manner which allows the first linear molecule to pass through the opening of the first cyclic molecule, and having at each end a first blocking group which is bulky enough to prevent the elimination of the first cyclic molecule, the second polyrotaxane having a second linear molecule and a second cyclic molecule, the second linear molecule having the second cyclic molecule included in a skewered manner which allows the second linear molecule to pass through the opening of the second cyclic molecule, and having at each end a second blocking group which is bulky enough to prevent the elimination of the second cyclic molecules, each opening of the first and second cyclic molecule is substantially cyclic, and the crosslinked polyrotaxane is formed by linking at least one of the first cyclic molecules and at least one of the second cyclic molecules via chemical bonding.

<5> In any one of items <1> to <4>, the first linear molecule may have at least two first cyclic molecules included in a skewered manner and the second linear molecule may have at least two second cyclic molecules included in a skewered manner.

<6> In any one of items <1> to <5>, the first linear molecule may have the first cyclic molecules included in a skewered manner at an amount of 0.001 to 0.6, preferably 0.01 to 0.5, more preferably 0.05 to 0.4 of a first maximum inclusion amount, which is defined as an amount at which the first cyclic molecule can be included at the maximum when the first linear molecule has the first cyclic molecule included in a skewered manner, and the value at maximum is normalized to be 1; and the second linear molecule may have the second cyclic molecules included in a skewered manner at an amount of 0.001 to 0.6, preferably 0.01 to 0.5, more preferably 0.05 to 0.4 of a second inclusion amount, which is defined as an amount at which the second cyclic molecule can be included at maximum when the second linear molecule has the second cyclic molecule included in a skewered manner, and the amount at maximum is normalized to be 1.

<7> In any one of items <1> to <6>, the first cyclic molecule and the second cyclic molecule may be the same or different.

<8> In any one of items <1> to <7>, the first linear molecule and the second linear molecule may be the same or different.

<9> In any one of items <1> to <8>, the first linear molecule and/or the second linear molecule may have a molecular weight of not less than 1,000, for example, 1,000 to 1,000,000, preferably not less than 5,000, for example, 5,000 to 1,000,000 or 5,000 to 500,000, and more preferably not less than 10,000, for example, 10,000 to 1,000,000, 10,000 to 500,000, or 10,000 to 300,000.

<10> In any one of items <1> to <9>, the first blocking group and the second blocking group may be the same or different.

<11> In any one of items <1> to <10>, the first blocking groups at one end and at another end of the first linear molecule may be the same or different, and the second blocking groups at one end and at another end of the second linear molecule may be the same or different.

<12> In any one of items <1> to <11>, the first and/or the second cyclic molecule may be selected from the group consisting of cyclodextrins, crown ethers, benzocrowns, dibenzo-crowns and dicyclohexano-crowns.

<13> In any one of items <1> to <12>, the first and/or the second linear molecule may be selected from the group consisting of polyethylene glycols, polyisoprene, polyisobutylene, polybutadiene, polypropylene glycols, polytetrahydrofuran, polydimethylsiloxane, polyethylene and polypropylene.

<14> In any one of items <1> to <13>, the blocking group may be selected from the group consisting of dinitrophenyl groups, cyclodextrins, adamantane groups, trityl groups, fluoresceins and pyrenes.

<15> In any one of items <1> to <14>, the blocking group may be a backbone or a side chain of a macromolecule having a molecular weight of 1,000 to 1,000,000.

<16> In any one of items <1> to <15>, at least one of the first cyclic molecules and at least one of the second cyclic molecules may be chemically bonded by a crosslinking agent.

<17> In item <16>, the crosslinking agent may have a molecular weight of less than 2,000, preferably less than 1,000, more preferably less than 600, and most preferably less than 400.

<18> In item <16> or <17>, the crosslinking agent may be selected from the group consisting of cyanuric chloride, trimesoyl chloride, terephthaloyl chloride, epichlorohydrin, dibromobenzene, glutaraldehyde, phenylene diisocyanates, tolylene diisocyanates, divinylsulfone, 1,1-carbonyldiimidazole and alkoxysilanes.

<19> In any one of items <1> to <18>, the cyclic molecules may be alpha-cyclodextrin, the linear molecule may be polyethylene glycol, the blocking group may be a dinitrophenyl group, and the crosslinking agent may be cyanuric chloride.

<20> In any one of items <1> to <19>, the compound may be an elastic material or a solvent-absorbing material.

<21> In any one of items <1> to <19>, the compound may be a viscoelastic material or a solvent-absorbing material.

<22> Crosslinked polyrotaxane comprising at least two polyrotaxane molecules, each of which has a polyethylene glycol molecule and an alpha-cyclodextrin molecule, the polyethylene glycol molecule having the alpha-cyclodextrin molecule included in a skewered manner which allows the polyethylene glycol molecule to pass through the opening of the alpha-cyclodextrin molecule, and having at each end a blocking group which is placed so as to prevent the elimination of the alpha-cyclodextrin molecule, wherein the crosslinked polyrotaxane is formed by linking the alpha-cyclodextrin molecule of each of the two polyrotaxane molecules to each other via chemical bonding.

<23> In item <22>, the crosslinked polyrotaxane may comprise a first blocking group having bulkiness and/or ionic property, thereby preventing the elimination of the first cyclic molecule.

<24> In item <22> or <23>, the crosslinked polyrotaxane may comprise a second blocking group having bulkiness and/or ionic property, thereby preventing the elimination of the second cyclic molecule.

<25> Crosslinked polyrotaxane comprising at least two polyrotaxane molecules, each of which has a polyethylene glycol molecule and an alpha-cyclodextrin molecule, the polyethylene glycol molecule having the alpha-cyclodextrin molecule included in a skewered manner which allows the polyethylene glycol molecule to pass through the opening of the alpha-cyclodextrin molecule, and having at each end a blocking group which is bulky enough to prevent the elimination of the alpha-cyclodextrin molecule, wherein the crosslinked polyrotaxane is formed by linking the alpha-cyclodextrin molecules of each of the two polyrotaxane molecules to each other via chemical bonding.

<26> In any one of items <22> to <25>, each of the two polyrotaxane molecules may have at least two alpha-cyclodextrin molecules included in a skewered manner by means of a single polyethylene glycol molecule.

<27> In any one of items <22> to <26>, the polyethylene glycol molecule may have the alpha-cyclodextrin molecules included in a skewered manner at an amount of 0.001 to 0.6, preferably 0.01 to 0.5, more preferably 0.05 to 0.4 of a maximum inclusion amount, which is defined as an amount at which alpha-cyclodextrin molecules can be included at maximum when a polyethylene glycol molecule has plural alpha-cyclodextrin molecules included in a skewered manner, and the amount at maximum is normalized to be 1.

<28> In any one of items <22> to <27>, the blocking group may be selected from the group consisting of dinitrophenyl groups, cyclodextrins, adamantane groups, trityl groups, fluoresceins and pyrenes.

<29> In any one of items <22> to <28>, the polyethylene glycol molecule may have a molecular weight of not less than 1,000, for example, 1,000 to 1,000,000, preferably not less than 5,000, for example, 5,000 to 1,000,000 or 5,000 to 500,000, and more. preferably not less than 10,000, for example, 10,000 to 1,000,000, 10,000 to 500,000, or 10,000 to 300,000.

<30> In any one of items <22> to <29>, the blocking group may be a backbone or a side chain of a macromolecule having a molecular weight of 1,000 to 1,000,000.

<31> In any one of items <22> to <30>, the chemical bonding may be formed by means of a crosslinking agent.

<32> In item <31>, the crosslinking agent may have a molecular weight of less than 2,000, preferably less than 1,000, more preferably less than 600, and most preferably less than 400.

<33> In item <31> or <32>, the crosslinking agent may be selected from the group consisting of cyanuric chloride, trimesoyl chloride, terephthaloyl chloride, epichlorohydrin, dibromobenzene, glutaraldehyde, phenylene diisocyanates, tolylene diisocyanates, divinylsulfone, 1,1-carbonyldiimidazole and alkoxysilanes.

<34> In any one of items <22> to <33>, the crosslinked polyrotaxane may be an elastic material or a solvent-absorbing material.

<35> In any one of items <22> to <33>, the crosslinked polyrotaxane may be a viscoelastic material or a solvent-absorbing material.

<36> A process for producing a compound comprising crosslinked polyrotaxane, comprising the steps of: mixing a cyclic molecule and a linear molecule to prepare polyrotaxane in which the linear molecule has the cyclic molecule included in a skewered manner which allows the linear molecule to pass through the opening of the cyclic molecules, blocking each end of the linear molecule with a blocking group so as to prevent the elimination of the cyclic molecule from the skewered state, and crosslinking two or more polyrotaxanes by linking the cyclic molecules to each other via chemical bonding, and wherein each opening of the cyclic molecules is substantially cyclic.

<37> A process for producing a compound comprising crosslinked polyrotaxane, comprising the steps of: mixing a cyclic molecule and a linear molecule to prepare polyrotaxane in which the linear molecule has the cyclic molecule included in a skewered manner which allows the linear molecule to pass through the opening of the cyclic molecule, blocking each end of the linear molecule with a blocking group so as to prevent the elimination of the cyclic molecules from the skewered state, and crosslinking two or more polyrotaxanes by linking the cyclic molecules to each other via chemical bonding.

<38> In the process of item <36> or <37>, the blocking group at each end of the linear molecule may be the same or different.

<39> In the process of any one of items <36> to <38>, the blocking group may have bulkiness and/or ionic property, so as to prevent the elimination of the cyclic molecules from the skewered state.

<40> In the step of preparing polyrotaxane of the process of any one of items <36> to <39>, the preparing conditions may be set and/or controlled, such that at least two cyclic molecules are included in a skewered manner by means of a single linear molecule. The preparing conditions may include dissolving excess of the linear molecules in saturated solution of the cyclic molecules, in addition to the preparation time and temperature.

<41> In the step of preparing polyrotaxane of the process of any one of items <36> to <40>, the preparing conditions may be controlled, such that the linear molecule has the cyclic molecules included in a skewered manner at an amount of 0.001 to 0.6, preferably 0.01 to 0.5, and more preferably 0.05 to 0.4 of a maximum inclusion amount, which is defined as an amount at which the cyclic molecule can be included at maximum when the linear molecule has the cyclic molecules included in a skewered manner, and the amount at maximum is normalized to be 1. The preparing conditions may include dissolving excess of the linear molecules in saturated solution of the cyclic molecules, in addition to the preparation time and temperature.

<42> In the process of any one of items <36> to <41>, the compound may be an elastic material or a solvent-absorbing material.

<43> In the process of any one of items <36> to <41>, the compound may be a viscoelastic material or a solvent-absorbing material.

<44> A process for producing a compound comprising crosslinked polyrotaxane, comprising the steps of mixing alpha-cyclodextrin and polyethylene glycol to prepare polyrotaxane in which the polyethylene glycol has the alpha-cyclodextrin included in a skewered manner which allows the polyethylene glycol to pass through the opening of the alpha-cyclodextrin, blocking each end of the polyethylene glycol molecule with a blocking group so as to prevent the elimination of the alpha-cyclodextrins from the skewered state, and crosslinking two or more polyrotaxane molecules by linking the alpha-cyclodextrins to each other via chemical bonding.

<45> In the process of item <44>, the blocking group may have bulkiness and/or ionic property, so as to prevent the elimination of the cyclic molecule from the skewered state.

<46> In the step of preparing polyrotaxane of the process of item <44> or <45>, the preparing conditions may be set and/or controlled, such that at least two alpha-cyclodextrin molecules are included in a skewered manner by means of the single polyethylene glycol molecule. The preparing conditions may include dissolving excess of the polyethylene glycol molecules in saturated alpha-cyclodextrin solution, in addition to the preparation time and temperature.

<47> In the step of preparing polyrotaxane of the process of any one of items <44> to <46>, the preparing conditions may be controlled, such that the polyethylene glycol molecule has the alpha-cyclodextrin included in a skewered manner at an amount of 0.001 to 0.6, preferably 0.01 to 0.5, and more preferably 0.05 to 0.4 of a maximum inclusion amount, which is defined as an amount at which alpha-cyclodextrin(s) can be included at maximum when the polyethylene glycol molecule has alpha-cyclodextrin(s) included in a skewered manner, and the amount at maximum is normalized to be 1. The preparing conditions may include dissolving excess of polyethylene glycol in saturated alpha-cyclodextrin solution, in addition to the preparation time and temperature.

<48> In the process of any one of items <44> to <47>, the compound may be an elastic material or a solvent-absorbing material.

<49> In the process of any one of items <44> to <47>, the compound may be a viscoelastic material or a solvent-absorbing material.

<50> A process for producing a compound comprising crosslinked polyrotaxane, comprising the steps of: providing a bicyclic molecule with a first and second substantially cyclic moieties, mixing the bicyclic molecule with a first linear molecule and a second linear molecule to prepare crosslinked polyrotaxane in which the first linear molecule has the bicyclic molecule included in a skewered manner which allows the first linear molecule to pass through the opening of the first ring of the bicyclic molecule, and the second linear molecule has the bicyclic molecule included in a skewered manner which allows the second linear molecule to pass through the opening of the second ring of the bicyclic molecule, and which is formed by linking the bicyclic molecules; and blocking each end of the linear molecules with a blocking group so as to prevent the elimination of the bicyclic molecules from the skewered state.

<51> In the process of item <50>, the first and second linear molecules may be the same or different.

<52> In the process of item <50> or <51>, the first linear molecule and/or the second linear molecule may have a molecular weight of not less than 1,000, for example, 1,000 to 1,000,000, preferably not less than 5,000, for example, 5,000 to 1,000,000 or 5,000 to 500,000, and more preferably not less than 10,000, for example, 10,000 to 1,000,000, 10,000 to 500,000, or 10,000 to 300,000.

<53> In the process of any one of items <50> to <52>, the first and/or second substantial ring may be an open ring, and before and/or after the blocking step, the process may comprise the step of closing the open ring.

<54> In the process of any one of items <50> to <53>, the blocking group at each end of the linear molecule may be the same or different.

<55> In the process of any one of items <50> to <54>, the blocking group may have bulkiness and/or ionic property, so as to prevent the elimination of the cyclic molecules from the skewered state.

<56> In the step of preparing crosslinked polyrotaxane of the process of any one of items <50> to <55>, one linear molecule may have at least two bicyclic molecules included in a skewered manner. Preparing conditions may be controlled, such that one linear molecule may have at least two bicyclic molecules included in a skewered manner. The preparing conditions may include dissolving excess of the linear molecules in a saturated solution of the cyclic molecules, in addition to the preparation time and temperature.

<57> In the step of preparing crosslinked polyrotaxane of the process of any one of items <50> to <55>, the bicyclic molecule may be included in a skewered manner through the linear molecule at an amount of 0.001 to 0.6, preferably 0.01 to 0.5, more preferably 0.05 to 0.4 of a maximum inclusion amount, which is defined as an amount at which the bicyclic molecule(s) can be included at maximum, when the linear molecule has the bicyclic molecule(s) included in a skewered manner, and the amount at maximum is normalized to be 1.

<58> In the process of any one of items <50> to <57>, the compound may be an elastic material or a solvent-absorbing material.

<59> In the process of any one of items <50> to <57>, the compound may be a viscoelastic material or a solvent-absorbing material.

<60> A compound comprising crosslinked polyrotaxane formed by crosslinking a first polyrotaxane and a second polyrotaxane, wherein the first polyrotaxane has a first linear molecule and a first cyclic molecule, the first linear molecule having the first cyclic molecule included in a skewered manner which allows the first linear molecule to pass through the opening of the first cyclic molecule, and having at each end a first blocking group which is placed so as to prevent the elimination of the first cyclic molecule, the second polyrotaxane has a second linear molecule and a second cyclic molecule, the second linear molecule having the second cyclic molecule included in a skewered manner which allows the second linear molecule to pass through the opening of the second cyclic molecule, and having at each end a second blocking group which is placed so as to prevent the elimination of the second cyclic molecule, each ring of the first and second cyclic molecules is substantially cyclic, and the crosslinking is formed via chemical bonding between at least one of the first cyclic molecules and at least one of the second cyclic molecules, and wherein the first cyclic molecule is movable between the ends of the first linear molecule, and the second cyclic molecule is movable between the ends of the second linear molecule, so that when force is applied to the compound, the first and second cyclic molecules are moved, so as for the force to be equally dispersed, whereby providing the compound having viscoelastic property.

<61> In the compound comprising crosslinked polyrotaxane of any one of items <1> to <19>, the first cyclic molecule is movable between the ends of the first linear molecule, the second cyclic molecule is movable between the ends of the second linear molecule, so that when force is applied to the compound, the first cyclic and second cyclic molecules are moved, so as for the force to be equally dispersed, whereby providing the compound having viscoelastic property.

<62> A compound comprising crosslinked polyrotaxane formed by crosslinking a first polyrotaxane and a second polyrotaxane, wherein the first polyrotaxane has a first linear molecule and a first cyclic molecule, the first linear molecule having the first cyclic molecule included in a skewered manner which allows the first linear molecule to pass through the opening of the first cyclic molecule, and having at each end a first blocking group which is placed so as to prevent the elimination of the first cyclic molecule, the second polyrotaxane has a second linear molecule and a second cyclic molecule, the second linear molecule having the second cyclic molecule included in a skewered manner which allows the second linear molecule to pass through the opening of the second cyclic molecule, and having at each end a second blocking group which is placed so as to prevent the elimination of the second cyclic molecule, each ring of the first and second cyclic molecules is substantially cyclic, and the crosslinking is formed via chemical bonding between at least one of the first cyclic molecules and at least one of the second cyclic molecules, and wherein the viscoelastic property of the compound is controlled by adjusting any one selected from the group consisting of: an amount of the first cyclic molecule(s) to be included through the first linear molecule; an amount of the second cyclic molecule(s) to be included through the second linear molecule; molecular weight and rigidity of the first and second linear molecules; and degrees of crosslinking between the first cyclic molecule and the second cyclic molecule.

<63> In the compound of any one of items <1> to <19>, the viscoelastic property of the compound is controlled by adjusting any one selected from the group consisting of: an amount of the first cyclic molecule(s) to be included through the first linear molecule; an amount of the second cyclic molecule(s) to be included through the second linear molecule; molecular weight and rigidity of the first and second linear molecules; and degrees of crosslinking between the first cyclic molecule and the second cyclic molecule.

<64> A contact lens comprising the compound according to any one of items <1> to <19> and <60> to <63>.

<65> A biomaterial comprising the compound according to any one of items <1> to <19> and <60> to <63>.

<66> A medical material comprising the compound according to any one of items <1> to <19> and <60> to <63>.

<67> A tire comprising the compound according to any one of items <1> to <19> and <60> to <63>.

<68> A coating material comprising the compound according to any one of items <1> to <19> and <60> to <63>.

<69> An adhesive comprising the compound according to any one of items <1> to <19> and <60> to <63>.

<70> In the crosslinked polyrotaxane according to any one of items <22> to <33>, wherein the alpha-cyclodextrin molecules are movable between ends of the polyethylene glycol molecule, and when force is applied to the crosslinked polyrotaxane, the alpha-cyclodextrin molecules are moved relatively to the polyethylene glycol molecule, so that the force can be equally dispersed, whereby providing the crosslinked polyrotaxane having viscoelastic property.

<71> In the crosslinked polyrotaxane according to any one of items <22> to <33>, the viscoelastic property of the crosslinked polyrotaxane is controlled by adjusting any one selected from the group consisting of: an amount of the alpha-cyclodextrin molecule(s) to be included through the polyethylene glycol molecule; molecular weight and rigidity of the polyethylene glycol; and degrees of crosslinking between the alpha-cyclodextrin molecules.

<72> A contact lens comprising the compound according to any one of items <22> to <33>, and <70> and <71>.

<73> A biomaterial comprising the compound according to any one of items <22> to <33>, and <70> and <71>.

<74> A medical material comprising the compound according to any one of items <22> to <33>, and <70> and <71>.

<75> A tire comprising the compound according to any one of items <22> to <33>, and <70> and <71>.

<76> A coating material comprising the compound according to any one of items <22> to <33>, and <70> and <71>.

<77> An adhesive comprising the compound according to any one of items <22> to <33>, and <70> and <71>.

BREIF DESCRIPTION OF THE DRAWINGS

DETAILED DESCRIPTION OF PREFERRED EMBODIMENTS

The present invention is now described in detail below.

A new compound according to the present invention is a compound that comprises or partially comprises crosslinked polyrotaxane having two or more polyrotaxane molecules and in which the cyclic molecules of the two or more polyrotaxane molecules are crosslinked via chemical bonding.

Figure 1:
FIG. 1 shows a schematic view of a polyrotaxane molecule.

Referring to FIG. 1, a new compound according to the present invention is explained specifically. FIG. 1 is a view illustrating schematically a polyrotaxane molecule contained in a compound according to the present invention. In FIG. 1, the polyrotaxane molecule 1 has two or more cyclic molecules 3 as a "rotator", a linear molecule 5 as the "axis" which has the cyclic molecules included in a skewered manner which allows the linear molecule 5 to pass through the opening of each of the cyclic molecules 3, and blocking groups 7 which are placed at the ends of the linear molecule 5 so as to prevent the elimination of the cyclic molecules 3 which are in a skewered state. A compound according to present invention comprises two or more polyrotaxane molecules of this type.

"Polyrotaxane" or "polyrotaxane molecule" herein refers to a molecule which has a cyclic molecule(s) as a "rotator" and a linear molecule as the "axis" and in which the cyclic and linear molecules are assembled such that the linear molecule has the cyclic molecule(s) included via non-covalent bonding in a skewered manner which allows the linear molecule to pass through the opening of each of the cyclic molecule(s). "Blocked polyrotaxane (molecule)" refers to a molecule in which each end of the linear molecule of a "polyrotaxane (molecule)" is blocked with a blocking group.

A linear molecule 5 may have at least two cyclic molecules 3. A linear molecule 5 may have cyclic molecules 3 at an amount of 0.001 to 0.6, preferably 0.1 to 0.5, and more preferably 0.05 to 0.4 of a maximum inclusion amount. The maximum inclusion amount is determined as an amount at which the linear molecule 5 has cyclic molecules 3 at the maximum in theory, and the amount is normalized to be 1.

Figure 2:
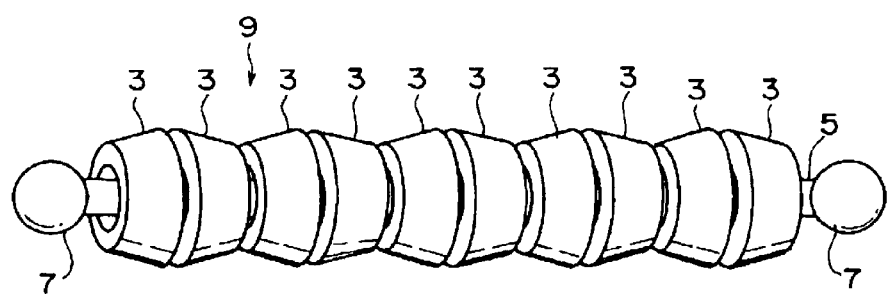
FIG. 2 shows a schematic view of a conventional polyrotaxane molecule in which cyclic molecules are filled at the maximum.

FIG. 2 is a schematic view illustrating a polyrotaxane molecule 9 in which a linear molecule 5 has cyclic molecules 3 at the maximum. Therefore, it is preferable that a compound according to the present invention utilizes a clathrate inclusion compound having cyclic molecules 3 filled in a sparse manner as in the case of polyrotaxane molecule 1 in FIG. 1, rather than in a dense manner as in the case of polyrotaxane molecule 9 in FIG. 2.

Furthermore, a new compound according to the present invention comprises two or more polyrotaxane molecules 1 as shown in FIG. 1, the cyclic molecules 3 of which are linked or crosslinked to each other via chemical bonding.

Figure 3:
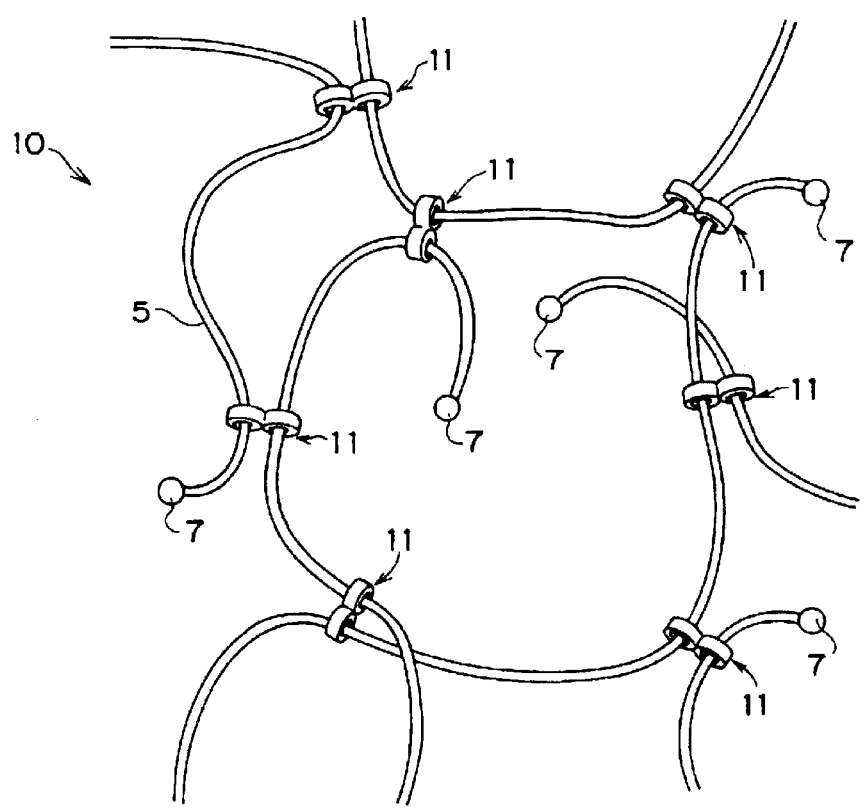
FIG. 3 shows a schematic view of the crosslinked polyrotaxane according to the present invention.

FIG. 3 is a view illustrating schematically crosslinked polyrotaxane 10, a new compound according to the present invention. In FIG. 3, a crosslinked cyclic molecule 11, which is formed by linking or crosslinking two cyclic molecules 3 via chemical bonding, results in crosslinking two or more polyrotaxane molecules 1 to form crosslinked polyrotaxane 10.

The compounds according to the present invention also include, within the scope of the present invention, compounds which partially comprise said crosslinked polyrotaxane 10.

Crosslinked polyrotaxane 10 according to the present invention, as shown in FIG. 3, has no directly crosslinking point between the linear molecules, and its geometric constraints result in gelling. Therefore, crosslinked polyrotaxane 10 has a different structure from one having directly crosslinking points as in conventional physical or chemical gels. Accordingly, the compounds according to the present invention can provide new gels or compounds having various properties which are different from those of conventional gels.

Specifically, when stress is applied to the compound of the present invention, the internal stress within the compound will be dispersed, because the compound has no directly crosslinking point between the polymers, whereby high fracture strength can be provided. Additionally, also in swelling, the linear molecules can form a network structure efficiently, whereby uniform and high swelling properties can be provided. The following will explain in more detail characteristics of the compounds according to the present invention.

In FIG. 1, cyclic molecules 3 and a linear molecule 5 are in an inclusion state where they are assembled without covalent bonding and the cyclic molecules 3 can be easily moved in the directions A between the ends of the linear molecule 5. In particular, if a linear molecule 5 with a high molecular weight has cyclic molecules 3 included in a sparse manner, the movement of the cyclic molecules 3 in the directions A can be made more easily. From a relative viewpoint, on the other hand, the polyrotaxane molecule 1 in FIG. 1 is in a state where the linear molecule 1 can be easily moved, if the cyclic molecules are fixed. Accordingly, as shown in FIG. 3, even though the cyclic molecules 3 form crosslinked cyclic molecules 11, the linear molecule 5 moves easily.

Figure 4:
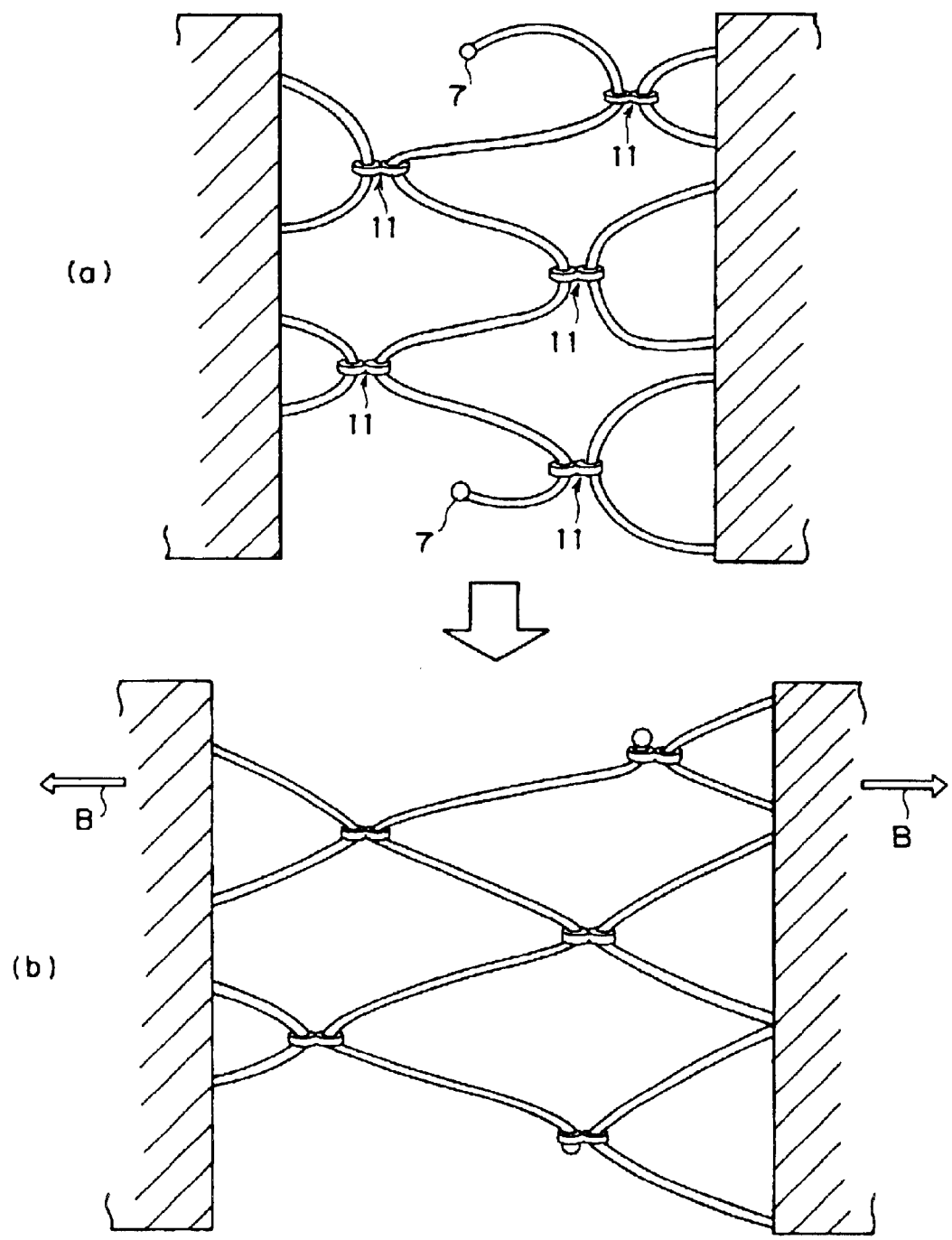
FIG. 4 is an illustrating figure showing that the crosslinked polyrotaxane according to the present invention has high fracture strength.

The compounds according to the present invention having such action allow the crosslinked cyclic molecules 11 or the linear molecules 5 to be easily moved, so that the internal stress can be uniformly dispersed, even when stress is applied in the directions B as shown in FIG. 4. In consequence, the gels or compounds of the present invention can be provided with high fracture strengths. In addition, the compounds of the present invention, in which higher entropic elasticity is derived from the structure of the crosslinked polyrotaxane 10 as shown in FIG. 3, can provide compounds having much higher entropic elasticity than those of conventional physical gels. In summary, the gels or compounds according to the present invention can provide materials exhibiting high fracture strength, superior expandability, superior restoring property, and/or very high entropy elasticity.

Moreover, by deblocking their blocking group, the compounds according to the present invention can be decomposed into cyclic molecules, non-crosslinked cyclic molecules, linear molecules, and blocking groups. As mentioned above, this means that the cyclic molecules or linear molecules can be easily moved in a relative manner. Removal of the blocking groups allows the cyclic molecules to eliminate from the linear molecules and to be free of the skewered state and the compounds according to the present invention are decomposed into their component substances.

For example, 1) it is possible that each of the decomposed components is recovered and recycled with ease. Also, 2) respective components are composed of biodegradable molecules, whereby the compounds of the present invention can be disposed of easier. That is, the compounds or gels according to the present invention can provide so-called "environment-friendly" ones which are effective, for example, for preservation of the environment.

The compounds according to the present invention also exhibit high hygroscopic and water-absorption properties, depending on cyclic molecules and linear molecules employed. That is, the compounds according to the present invention will exhibit high hygroscopic and water-absorption properties, by means of employing hydrophilic molecules as the cyclic molecules and linear molecules, or employing hydrophilic compounds as compounds which partially comprise the crosslinked polyrotaxane according to the present invention. In the case where the compounds according to the present invention are derived from the structure of the crosslinked polyrotaxane 10 shown in FIG. 3 and display water-absorption and hygroscopic properties, uniform expansion will take place. Such uniform expansion can not be realized in conventional polymers or gels having high water-absorption properties, or the like.

The following will give a detailed explanation of linear molecules, cyclic molecules and blocking groups contained in the compounds according to the present invention, as well as linking or crosslinking between the cyclic molecules.

Linear Molecules

A linear molecule contained in a compound according to the present invention is a molecule or substance which can be included by means of the ring portion of cyclic molecules and united with the cyclic molecules via non-covalent bonding, and not limited to particular molecules, as long as it is linear. In the present invention, a "linear molecule" refers to a molecule, including macromolecules, and any other substance which satisfies the above-described requirement.

In the present invention, "linear" in the term "linear molecule" means to be of substantial "linear" chain. This means that a linear molecule may have a branched chain or chains, as long as cyclic molecules that are rotators are rotatable, or a linear molecule allows cyclic molecules to be slidable or movable thereon. The length of "linear" chain of a linear molecule is not limited to a particular length, as long as a linear molecule allows cyclic molecules to be slidable or movable thereon.

In addition, "linear" in the term "linear molecule" herein is specified relatively, in relation to compounds partially comprising crosslinked polyrotaxane according to the present invention. That is, in the case of a compound partially comprising crosslinked polyrotaxane, the compound contains a portion of the crosslinked polyrotaxane; a linear molecule is contained in said crosslinked polyrotaxane. Accordingly, a linear molecule can constitute a very small portion in a compound. Even though a linear molecule constitutes a very small portion, the length of "linear" chain has no limitation in particular as described above, as long as a linear molecule allows cyclic molecules to be slidable or movable thereon.

Linear molecules in the present invention can include hydrophilic polymers such as polyvinyl alcohol and polyvinylpyrrolidone, poly(meth)acrylic acid, cellulose-derived resins (carboxymethylcellulose, hydroxyethylcellulose, hydroxypropylcellulose and the like), polyacrylamide, polyethylene oxide, polyethylene glycols, polyvinyl acetal-derived resins, polyvinyl methyl ether, polyamines, polyethyleneimine, casein, gelatin, starch and the like, and/or copolymers thereof; hydrophobic polymers such as polyolefinic resins such as polyethylene, polypropylene and copolymer resins with other olefinic monomers, polyester resins, polyvinyl chloride resins, polystyrene-derived resins such as polystyrene and acrylonitrile-styrene copolymers, polymethyl methacrylate and (meth)acrylate ester copolymers, acrylic resins such as acrylonitrile-methyl acrylate copolymer resins, polycarbonate resins, polyurethane resins, vinyl chloride-vinyl acetate copolymer resins, polyvinyl butyral resins; and derivatives or modifications thereof.

Among these compounds, preferred are polyethylene glycols, polyisoprene, polyisobutylene, polybutadiene, polypropylene glycols, polytetrahydrofuran, polydimethylsiloxane, polyethylene, and polypropylene, and particularly preferred are polyethylene glycols.

It is preferable that the linear molecules in the present invention themselves have high fracture strength. The fracture strength of compounds or gels depends on the binding strength between the blocking group and linear molecule, the binding strength between the cyclic molecules, and other factors, and thus if a linear molecules in the present invention itself has a high fracture strength, the compounds or gels can provide a higher fracture strength.

The linear molecules in the present invention preferably have molecular weights of not less than 1,000, for example, 1,000 to 1,000,000, preferably not less than 5,000, for example 5,000 to 1,000,000 or 5,000 to 500,000, and more preferably not less than 10,000, for example, 10,000 to 1,000,000, 10,000 to 500,000, or 10,000 to 300,000.

In addition, it is preferable in terms of being "environment-friendly" that the linear molecules in the present invention are biodegradable molecules as described above.

The linear molecules in the present invention preferably have reactive groups at each end. Having reactive groups allows facilitating the reaction with blocking groups. Reactive groups depend on blocking groups to be employed. Examples thereof can include hydroxyl, amino, carboxyl, thiol groups and the like.

Cyclic Molecules

A cyclic molecule in the present invention can utilize any cyclic molecule, as long as it is cyclic molecule capable of forming an inclusion with the above-described linear molecules.

In the present invention, a "cyclic molecule" means one of a variety of cyclic substances including cyclic molecules. In the present invention, a "cyclic molecule" also means a molecule or substance which is substantially cyclic or of substantial ring. That is, the term "substantially cyclic" or "substantial ring" means to include molecules in which the ring is not closed completely, as in the letter "C", and molecules having a helical structure in which as in the letter "C", one end and the other end are not connected and placed in a piled manner. Furthermore, the ring of a "bicyclic molecule" discussed below can also be defined similarly to the case where a "cyclic molecule" is "substantially cyclic" or of "substantial ring". In other words, one ring or both rings of a "bicyclic molecule" may be closed incompletely as in the letter "C" or form a helical structure in which as in the letter "C", one end and the other end are not connected and placed in a piled manner.

Examples of cyclic molecules in the present invention may include various cyclodextrins (for example, alpha-cyclodextrin, beta-cyclodextrin, gamma-cyclodextrin, dimethylcyclodextrin and glucosylcyclodextrin, derivatives and modifications thereof), crown ethers, benzo-crowns, dibenzo-crowns, and dicyclohexano-crowns, and derivatives and modifications thereof.

The above-described cyclodextrins, crown ethers and the like have different opening dimensions of the cyclic molecules, depending on their type. Thus, a cyclic molecule to be employed can be selected, depending on the type of an employed linear molecule, the hydrophilicity or hydrophobicity of a linear molecule, and the like, specifically, the diameter of the cross-section of a cylinder in the case where an employed linear molecule is considered to be cylindrical. When a cyclic molecule with a relatively large opening and a cylindrical linear molecule with a relatively small diameter are used, two or more linear molecules can be included through the opening of the cyclic molecule.

Among these molecules, cyclodextrins are biodegradable and thus preferred in that they are "environment-friendly" as described above.

It is preferable to use alpha-cyclodextrin as a cyclic molecule and polyethylene glycol as a linear molecule.

Cyclic molecules in the present invention preferably have reactive groups on the outside of their ring. This allows the reaction to be carried out with ease using the reactive groups, when cyclic molecules are linked or crosslinked. Reactive groups, depending on blocking groups to be employed and others, can include, for example, hydroxyl, amino, carboxyl, thiol groups, and the like. In addition, it is preferable to employ groups which do not react with the blocking groups during the above-described blocking reaction.

Blocking Groups

Blocking groups in the present invention can utilize any group, as long as they allow the cyclic molecules to be retained in a skewered form by means of the linear molecule. These moieties can include the groups having "bulkiness" and/or "ionic property," for example. The term "group" herein means one of various groups including molecule groups and macromolecule groups. That is, a group having "bulkiness" may be a group as shown schematically by a ball in FIG. 1, or a solid support as shown as a side wall in FIG. 4. Also, the linear molecule allows cyclic molecules to be retained in a skewered form by interacting the "ionic property" of a group having "ionic property" with the "ionic property" of the cyclic molecules having "ionic property," for example, by repelling them to each other.

In addition, blocking groups in the present invention may be the main chain or a side chain of a macromolecule, as long as they allow the skewered form to be retained, as described above. When a blocking group is a macromolecule A, a configuration can be possible in which there is the macromolecule A as a matrix, portion of which contains a compound according to the present invention, or conversely there is a compound according to the present invention as a matrix, portion of which contains the macromolecule A. Thus, composite materials having combined properties of a compound according to the present invention and a macromolecule A can be formed by combination with a macromolecule A having different properties.

Specifically, molecular blocking groups can include dinitrophenyl groups such as 2,4- and 3,5-dinitrophenyl groups; cyclodextrins; adamantane groups; trityl groups; fluoresceins and pyrenes; and derivatives and modifications thereof. More specifically, even in the case of employing alpha-cyclodextrin as a cyclic molecule and polyethylene glycol as a linear molecule, can be included cyclodextrins, dinitrophenyl groups, such as 2,4- and 3,5-dinitrophenyl groups, adamantane groups, trityl groups, fluoresceins and pyrenes, and derivatives and modifications thereof.

Crosslinked Cyclic Molecules

The compounds according to the present invention comprise two or more polyrotaxane molecules as shown in FIG. 1 and can be obtained by linking or crosslinking cyclic molecules 3 of respective polyrotaxanes.

Two or more polyrotaxane molecules to be used for crosslinking may be the same or different. Thus, a first polyrotaxane molecule can be linked or crosslinked to a second polyrotaxane molecule which is different from the first polyrotaxane molecule. A first polyrotaxane molecule has first cyclic molecules, and a second polyrotaxane molecule has second cyclic molecules, and thus the first cyclic molecules and the second cyclic molecules can be linked or crosslinked. In this case, the first cyclic molecules and the second cyclic molecules may be the same or different.

Preferably, the first cyclic molecules and the second cyclic molecules are crosslinked via chemical bonding. In this case, chemical bonding may be formed by a simple bond or by a bond mediated by various atoms or molecules.

A cyclic molecule preferably has one or more reactive groups on the outside of the ring, as described above. In particular, it is preferable that after a blocked polyrotaxane molecule is formed, the cyclic molecules are crosslinked to each other using a crosslinking agent. In this case, conditions for the crosslinking reaction should be conditions under which the blocking groups of the blocked polyrotaxane are not removed.

In addition, a first cyclic molecule can be linked or crosslinked to a second cyclic molecule which is different from the first cyclic molecule. A first and second cyclic molecules can posses one or more reactive groups with which respective cyclic molecules can be reacted to result in bonding.

The compounds according to the present invention can be degraded not only by removing the above-described blocking groups, but also by cleavage of crosslinking in the crosslinked cyclic molecules. In this case, cleavage of the crosslinking can yield two or more blocked polyrotaxanes. When a compound according to the present invention comprises components other than polyrotaxane, it is possible to recover the polyrotaxane released from crosslinking and other components.

As crosslinking agents which can be used in the present invention, one can employ crosslinking agents well known up to now. Examples may include cyanuric chloride, trimesoyl chloride, terephthaloyl chloride, epichlorohydrin, dibromobenzene, glutaraldehyde, phenylene diisocyanates, tolylene diisocyanates (for example, tolylene 2,4-diisocyanate), 1,1-carbonyldiimidazole, divinylsulfone and the like. Various types of coupling agents can also be included, such as silane coupling agents (for example, various alkoxysilanes) and titanium coupling agents (for example, various alkoxytitaniums). Additional examples can include various photocrosslinkers which are employed for materials designed for soft contact lenses, for example, photocrosslinkers based on stilbazolium salts such as formylstyrylpyridium salts (see, Ichimura, K. et al., Journal of Polymer science. Polymer chemistry edition 20, 1411–1432 (1982), incorporated herein by reference), and other photocrosslinkers, for example, photocrosslinkers by photo-dimerization, specifically, cinnamic acid, anthracene, thymines, and the like.

The cross-linking agents preferably have molecular weights of less than 2,000, preferably less than 1,000, more preferably less than 600, and most preferably less than 400.

In the case of using alpha-cyclodextrin as a cyclic molecule and using a crosslinking agent to crosslink it, examples of the crosslinking agent can include cyanuric chloride, tolylene 2,4-diisocyanate, 1,1-carbonyldiimidazole, trimesoyl chloride, terephthaloyl chloride, and alkoxysilanes such as tetramethoxysilane and tetraethoxysilane and the like. In particular, it is preferable to use alpha-cyclodextrin as a cyclic molecule and cyanuric chloride as a crosslinking agent.

The previous paragraphs have mainly described, as a crosslinked cyclic molecule according to the present invention, a substance formed by forming polyrotaxane, followed by crosslinking its cyclic molecules to each other. In addition to these embodiments, it is possible to utilize a substance having a crosslinked cyclic molecular structure, that is, a "bicyclic molecule" having a first ring and a second ring. In this case, crosslinked polyrotaxane according to the present invention can be obtained, for example, by mixing a "bicyclic molecule" and a linear molecule and allowing the linear molecule to be included in a skewered manner through the first and second rings of the "bicyclic molecule". Then, each end of the linear molecule can be blocked with a blocking group after inclusion.

The compounds according to the present invention can be prepared in the following way.

Firstly, a cyclic molecule and a linear molecule are mixed to prepare polyrotaxane in which the linear molecule is included in a skewered manner through the opening of the cyclic molecule. Upon mixing in this preparation step, various solvents can be utilized. Such solvents can include, for example, solvents in which cyclic molecule and/or linear molecule are dissolved or dispersed. Specifically, solvents can be selected as appropriate, depending on cyclic molecule and/or linear molecule employed in the present invention, and the like.

In the preparation of polyrotaxane, it is preferable to control the amount of cyclic molecule to be included in a skewered manner through a linear molecule. Preferably, a linear molecule has at least two cyclic molecules included in a skewered manner. Also, the amount of a cyclic molecule is preferably such that the cyclic molecule is present at a value of 0.001 to 0.6, preferably 0.01 to 0.5, and more preferably 0.05 to 0.4, of the maximum inclusion amount. The maximum inclusion amount is determined as an amount at which a linear molecule allows cyclic molecules to be included at the maximum and the value of the maximum inclusion amount is normalized to be 1.

The above-described amount of a cyclic molecule can be controlled by the mixing time, temperature, and pressure, increasing the molecular weight of a used linear molecule, and the like. More specifically, controlling involves, for example, dissolving an excess amount of a linear molecule in a saturated solution of a cyclic molecule.

For polyrotaxane according to the present invention, it is preferable that a linear molecule has cyclic molecules not filled in a dense state, as described above. By filling cyclic molecules in a non-dense state, it is possible to maintain movable lengths of the crosslinked molecules or the linear molecule, when crosslinked. These movable lengths can lead to high fracture strength, high entropic elasticity, superior expandability, and/or superior restoring property, and if desired, high absorbability or hygroscopicity.

Secondly, blocked polyrotaxane is prepared by blocking each end of the linear molecule with a blocking group so as to prevent the elimination of the cyclic molecules from the resulting polyrotaxane in the skewered state.

Two or more blocked polyrotaxanes are crosslinked by linking the cyclic molecules of the resulting blocked polyrotaxane via chemical bonding, to obtain crosslinked polyrotaxane.

A process for preparing a compound according to the present invention will be explained in more detail. Thus, there is given an explanation of a process for preparing a compound according to the present invention, in the case of using alpha-cyclodextrin as a cyclic molecule, polyethylene glycol as a linear molecule, 2,4-dinitrophenyl group as a blocking group, and cyanuric chloride as a crosslinking agent.

Firstly, for the purpose of a subsequent blocking treatment, each end of polyethylene glycol is converted into an amino group to obtain a polyethylene glycol derivative. Alpha-cyclodextrin and the polyethylene glycol derivative are mixed to prepare polyrotaxane. Upon preparation, for example, the mixing time can be set to be from 1 to 48 hours and the mixing temperature from 0 to 100° C., such that the inclusion amount of alpha-cyclodextrin to the polyethylene glycol derivative, whose maximum inclusion amount is normalized to be 1, reaches 0.001 to 0.6.

In general, a polyethylene glycol with an average molecular weight of 20,000 allows 230 alpha-cyclodextrin molecules to be included at the maximum. Accordingly, this value corresponds to the maximum inclusion amount. The above-described conditions are for inclusion of alpha-cyclodextrin at an amount of 60 to 65 (63) molecules on average, that is, at an amount of 0.26 to 0.29 (0.28) of the maximum inclusion amount. The inclusion amount of alpha-cyclodextrin can be determined by NMR, light absorption, elemental analysis, and the like.

The resulting polyrotaxane is subjected to the reaction with 2,4-dinitro-fluorophenylbenzene dissolved in DMF, thereby yielding blocked polyrotaxane.

Next, the resulting blocked polyrotaxane is dissolved in an aqueous solution of sodium hydroxide. To this solution is added cyanuric chloride, and the reaction was carried out to form crosslinked polyrotaxane in which alpha-cyclodextrins are crosslinked.

Alternatively, other than the above-described process, crosslinked polyrotaxane according to the present invention can be produced by the following process employing another cyclic molecule, a "bicyclic molecule". Firstly, bicyclic molecule is provided. As described above, the bicyclic molecule has a first and second substantial rings. Secondly, the bicyclic molecule and a first and second linear molecules are mixed to prepare crosslinked polyrotaxane in which the first linear molecule is included in a skewered manner through the opening of the first ring of the bicyclic molecule, the second linear molecule is included in a skewered manner through the opening of the second ring of the bicyclic molecule, and the crosslinking is formed via the bicyclic molecules. Thirdly, the resulting crosslinked polyrotaxane is subjected to a step in which each end of the linear molecules is blocked with a blocking group so as to prevent the elimination of the bicyclic molecule from a skewered state.

Although a bicyclic molecule is "bicyclic," it may have one or more cyclic moieties, besides a first and second substantially cyclic moieties. A bicyclic molecule may also be a molecule having a structure in which two segments like the letter "C" are linked. In this case, the "C"-like segments can be closed, after the linear molecule is included in a skewered manner, or after the linear molecule is blocked with a blocking group. For molecules having a structure in which two segments like the letter "C" are linked and by closing the arms of the letter "C" of the molecules, see Asakawa, M. et al., Angewante Chemie-International Edition 37(3), 333–337 (1998), and Asakawa, M. et al., European Journal of Organic Chemistry 5, 985–994 (1999), both are incorporated herein by reference.

EXAMPLES

The present invention is now illustrated more specifically by Examples. The following Examples are merely illustrative of specific embodiments of the present invention, but are not construed to limit the present invention thereto.

Example 1

<Activation of the Polyethylene Glycol Ends>

Into a 100 ml Erlenmeyer flask were placed 4 g of polyethylene glycol (abbreviated to PEG, an average molecular weight of 20,000) and 20 ml of dry methylene chloride, to dissolve PEG. The solution was placed under an argon atmosphere, 0.8 g of 1,1-carbonyldiimidazole was added, and subsequently under an argon atmosphere, the reaction was subjected to stirring at room temperature (20° C.) for 6 hours.

The product obtained in the previous step was poured into 300 ml of diethyl ether stirred at a high speed. After allowing the mixture to stand for 10 minutes, a solution containing precipitates was centrifuged at 10,000 rpm for 5 minutes. Precipitates were removed and dried under vacuum at 40° C. for 3 hours to give 3.74 g of the product.

The resulting product was dissolved in 20 ml of methylene chloride. This solution was added dropwise to 10 ml of ethylenediamine over 3 hours, and then stirred for 40 minutes. The resultant reaction mixture was subjected to a rotary evaporator to remove the methylene chloride. The residue was then dissolved in 50 ml of water, put into a dialysis tube (cut-off molecular weight of 8,000), and was subjected to dialysis against water for 3 days. The resulting dialyzate was dried with a rotary evaporator. The dried material was dissolved again in 20 ml of methylene chloride and re-precipitated using 180 ml of diethyl ether. A solution containing precipitates was centrifuged at 100,000 rpm for 5 minutes, and precipitates were dried under vacuum at 40° C. for 2 hours to give 2.83 g of the product having an amino group introduced at each end of PEG (abbreviated to DAT-PEG). Alternatively, commercially available polyethylene glycol-bisamine (abbreviated to PEG-BA) (produced by Fluka) can be utilized, instead of the resulting product.

<Preparation of Polyrotaxane>

After 3.6 g of alpha-cyclodextrin (abbreviated to alpha-CD) and 0.9 g of DAT-PEG (a molecular weight of about 20,000) were dissolved separately in 15 ml of water at 80° C., the solutions were mixed. Then, the mixture was stored at 5° C. for 6 hours to prepare polyrotaxane. Then, the product was dried under vacuum at 40° C. for 12 hours.

<Preparation of Blocked Polyrotaxane>

The polyrotaxane obtained above was placed into a 100 ml Erlenmeyer flask. A mixed solution of 10 ml of N,N-dimethylformamide and 2,4 ml of 2,4-dinitro-fluorobenzene was prepared separately, and added dropwise into the flask in which the polyrotaxane was contained. The reaction was carried out at room temperature under an argon atmosphere. After 5 hours, 40 ml of dimethylsulfoxide was added to the mixture to form a clear solution. This solution was added dropwise to 750 ml of water with vigorous stirring to yield pale yellow precipitates. The precipitates were dissolved again in 50 ml of dimethylsulfoxide, and the solution was added dropwise to 700 ml of 0.1% aqueous sodium chloride solution with vigorous stirring to cause re-precipitation. Precipitates were subjected to washing with water and methanol and centrifugation at 10,000 rpm for 1 minute after washing; washing and centrifugation were repeated three times, respectively. The resulting material was dried under vacuum at 50° C. for 12 hours to give 3.03 g of blocked polyrotaxane.

<The Amount of Alpha-CD within the Blocked Polyrotaxane>

The amount of alpha-CD within the resulting blocked polyrotaxane was determined by spectrometry and NMR.

Measurements revealed that one blocked polyrotaxane had 63 molecules of alpha-CD included. When the used PEG has alpha-CD filled closely, a maximum inclusion amount of 230 alpha-CDs can be calculated. This value and the measurements of spectrometry and NMR revealed that the amount of alpha-CD in the blocked polyrotaxane used in this example is 0.28 of the maximum inclusion amount.

<Preparation of Crosslinked Polyrotaxane>

One hundred milligrams of the blocked polyrotaxane was dissolved in 0.5 ml of 1N aqueous sodium hydroxide solution. To this solution was added a solution in which 35 mg of cyanuric chloride was dissolved in 0.5 ml of 1N aqueous sodium hydroxide solution, to start the crosslinking reaction. After 3 hours at room temperature, gelling was observed. The resultant gel was identified as a crosslinked polyrotaxane gel.

The gel obtained was a transparent yellow crosslinked polyrotaxane gel having an expansion coefficient of about 40 times in water.

Although the amount of PEG contained in the resultant gel was about 2.5% by weight, it was observed that the resultant gel bounded well, when the gel was caught by hand, and made to bound like a ball. In addition, applying tensile force to the gel resulted in twice or more expansion, and removal of the force restored the shape to its original shape.

When the gel was dried, followed by swelling the dried material with water, the dried gel swelled about 400 times the dry weight. This shows that the dried gel absorbed water about 1,600 times the amount of PEG contained in the gel.

<Degradation of the Crosslinked Polyrotaxane>

The gel obtained above was added to a strongly alkaline solution, i.e. a 1 N solution of sodium hydroxide in water, at a high temperature, i.e. 50□ C. The gel was dissolved in 7 hours. The resultant solution was analyzed on a High Performance Liquid Chromatography-Mass Spectrometer and the like, and found to contain DAT-PEG, 2,4-dinitrophenol, crosslinked alpha-CD, and alpha-CD (without crosslinkage). This shows that the crosslinked polyrotaxane was easily degraded into its respective components, when placed under conditions allowing removal of its blocking groups.

Example 2

Crosslinked polyrotaxane was obtained in a manner similar to that in Example 1, except that in <Preparation of crosslinked polyrotaxane> in Example 1, dimethylsulfoxide (DMSO) was used as a solvent, instead of 1 N aqueous sodium hydroxide solution. In preparing a solution of cyanuric chloride in DMSO in <Preparation of crosslinked polyrotaxane>, cyanuric chloride was dissolved in DMSO with keeping the temperature at 25° C. The gelling reaction required 2 hours at 50□ C.

The gel obtained exhibits high elasticity, superior expandability, superior restoring property, and high solvent-absorption, similarly to the gel obtained in Example 1.

Examples 3 to 5

Cross-linked polyrotaxane was prepared in a manner similar to that in Example 2, except that in stead of cyanuric chloride as a crosslinking agent, tetraethoxysilane was utilized in Example 3, 1,1-carbonyldiimidazole in Example 4, and tolylene 2,4-diisocyanate in Example 5.

The gels obtained exhibits high elasticity, superior expandability, superior restoring property, and high solvent-absorption, similarly to the gel obtained in Example 1.

Example 6

<Preparation of Polymer Having an Active Group at Each End>

Into a 100 ml Erlenmeyer flask were placed 4.0 g of PEG (an average molecular weight of 70,000) and 30 ml of dry methylene chloride, and the solution was placed under an argon atmosphere to dissolve PEG. 0.8 g of N,N-carbonyldiimidazole (CDI) was further added to this solution, and subsequently under an argon atmosphere, the reaction was subjected to stirring at room temperature (20□ C.) for 15 hours. Then, CDI-PEG was obtained in which both ends of the PEG were activated with carbonyldiimidazole.

Into a 300 ml Erlenmeyer flask was put 100 ml of diethyl ether and stirred at a high speed. The resulting solution was poured into the ether to precipitate CDI-PEG, which in turn was centrifuged. Precipitated CDI-PEG was washed twice with diethyl ether and dried under vacuum to give 3.81 g (dry weight) of CDI-PEG.

The resulting CDI-PEG was dissolved in 30 ml of methylene chloride to prepare a solution. To this solution, with stirring, was added dropwise 5 ml of ethylenediamine. Then, mixed solution was stirred for 5 hours.

The resultant solution was added dropwise to 200 ml diethyl ether stirred at a high speed, to precipitate DAT-PEG having an amino group at each end. After centrifugation, the product was dried under vacuum. The resultant dried product was further subjected to three times of precipitation and purification using methylene chloride and diethyl ether to give 2.82 g (dry weight) of DAT-PEG.

<Preparation of Polyrotaxane>

30 ml of water, 3.6 g of alpha-CD, and 1.2 g of DAT-PEG were heated at 80° C. for 1 hour to form a clear solution. Then, the solution was stored at 5□ C. for 12 hours to yield an inclusion complex paste.

A solution was prepared by dissolving 120 mg of sodium 2,4,6-trinitrobenzenesulfonate dihydrate in 6.0 ml of a borate pH standard solution (pH 9.2). This solution was mixed into the above-described inclusion paste and stirred. After 1 hour, additional 20 ml water was added, and the reaction was continued for additional 1 hour. The product was centrifuged and washed 5 times with 40 ml of water (80□ C.), followed by drying, to give 1.27 g of polyrotaxane.

<Gelling of the Polyrotaxane>

One hundred milligrams of the polyrotaxane obtained above was dissolved in 1 ml of dimethylsulfoxide (DMSO). To this solution was added 50 microliters of tetraethoxysilane. The mixture was reacted at 70□ C. for 12 hours, resulting in the formation of a transparent yellow gel. It was ascertained that the tetraethoxysilane was reacted with OH groups of alpha-CD in the polyrotaxane to crosslink alpha-CD molecules.

Industrial Applicability

The compounds comprising crosslinked polyrotaxane according to the present invention are applicable to various products due to their properties, for example, high absorbability, uniform expandability, and/or elasticity or viscoelasticity. For example, applications can include rubber bands, packing materials, agar mediums, cloths, cushioning materials for soles of shoes such as sport shoes, shock absorbing materials (bumpers) for automobiles and various devices, toys utilizing high water-absorption, coatings for rubbing portions of devices (for example, coatings for housings or sliding parts of pumps), adhesives, sealing materials for tight seal, dehumidifiers or dew drop removers utilizing hygroscopicity, fillers for bed mats resembling waterbeds, materials for special effects or models, soft contact lens materials (especially, soft contact lens materials having high water-content and/or superior strength), tire materials, electrophoretic gels, new foodstuffs corresponding to gums and others, gums for dogs, biomaterials such as artificial corneas, lenses, vitreous bodies, skins, muscles, joints, or cartilages, and also including biocompatible materials such as breast-implant materials, medical materials for external applying such as wet compress materials or wound dressings, drug delivery systems, earplugs, wet suits, protection mats placed on the outfield fence in a baseball stadium, arm rests for personal computers, disposable sanitary goods such as diapers for children, sanitary napkins or articles for adult incontinence, photographic sensitive materials, perfumes, applying materials such as coatings including various paints and the above-described coatings, functional membranes for separation, water-swellable rubbers, water-stop tapes, gabions or sandbags, materials for pile-extracting articles, materials for removing water in oil, moisture conditioning material, hygroscopic gelling materials, dehumidifiers, materials for artificial snow in an indoor artificial skiing slope, refractory coatings for buildings, materials for preventing debris avalanche, concrete products such as concrete-placing materials, sludge gelling agents, agents for preventing lost returns, tree-planting materials such as water-in-soil retaining agents or seedling mediums, materials for chromatographic carriers, materials for bioreactor carriers, or various component materials for fuel cells, for example, various cell materials such as electrolytes and the like.

What is claimed is:

1. A compound comprising crosslinked polyrotaxane, wherein the crosslinked polyrotaxane has a first and a second polyrotaxane, the first polyrotaxane having a first linear molecule and a first cyclic molecule, the first linear molecule having the first cyclic molecule included in a skewered manner which allows the first linear molecule to pass through the opening of the first cyclic molecule, and having at each end a first blocking group which is placed so as to prevent the elimination of the first cyclic molecule, the second polyrotaxane having a second linear molecule and a second cyclic molecule, the second linear molecule having the second cyclic molecule included in a skewered manner which allows the second linear molecule to pass through the opening of the second cyclic molecule, and having at each end a second blocking group which is placed so as to prevent the elimination of the second cyclic molecules, each opening of the first and second cyclic molecules is substantially cylic, and the crosslinked polyrotaxane is formed by linking at least one of the first cyclic molecules and at least one of the second cyclic molecules via chemical bonding.

2. The compound according to claim 1, wherein the first blocking group has bulkiness and/or ionic property, thereby preventing the elimination of the first cyclic molecules.

3. The compound according to claim 1, wherein the second blocking group has bulkiness and/or ionic property, thereby preventing the elimination of the second cyclic molecules.

4. A compound comprising crosslinked polyrotaxane, wherein the crosslinked polyrotaxane has a first and a second polyrotaxane, the first polyrotaxane having a first linear molecule and a first cyclic molecule, the first linear molecule having the first cyclic molecule included in a skewered manner which allows the first linear molecule to pass through the opening of the first cyclic molecule, and having at each end a first blocking group which is bulky enough to prevent the elimination of the first cyclic molecule, the second polyrotaxane having a second linear molecule and a second cyclic molecule, the second linear molecule having the second cyclic molecule included in a skewered manner which allows the second linear molecule to pass through the opening of the second cyclic molecule, and having at each end a second blocking group which is bulky enough to prevent the elimination of the second cyclic molecules, and the crosslinked polyrotaxane is formed by linking at least one of the first cyclic molecules and at least one of the second cyclic molecules via chemical bonding.

5. The compound according to claim 1, wherein the first linear molecule has at least two first cyclic molecules included in a skewered manner and the second linear molecule has at least two second cyclic molecules included in a skewered manner.

6. The compound according to claim 1,
wherein the first linear molecule has the first cyclic molecules included in a skewered manner at an amount of 0.001 to 0.6 of a first maximally includable amount, which is defined as an amount at which the first cyclic molecule can be maximally includable when the first linear molecule has the first cyclic molecule included in a skewered manner, and the maximally includable amount is normalized to be 1; and
the second linear molecule has the second cyclic molecules included in a skewered manner at an amount of 0.001 to 0.6 of a second inclusion amount, which is defined as an amount at which the second cyclic molecule can be maximally includable when the second linear molecule has the second cyclic molecule included in a skewered manner, and the maximally includable amount is normalized to be 1.

7. The compound according to claim 1, wherein the first cyclic molecule and the second cyclic molecule may be the same or different.

8. The compound according to claim 1, wherein the first linear molecule and the second linear molecule may be the same or different.

9. The compound according to claim 1, wherein the first linear molecule and/or the second linear molecule have/has a molecular weight of not less than 1,000, for example, 1,000 to 1,000,000, preferably not less than 5,000, for example, 5,000 to 1,000,000 or 5,000 to 500,000, and more preferably not less than 10,000, for example, 10,000 to 1,000,000, 10,000 to 500,000, or 10,000 to 300,000.

10. The compound according to claim 1, wherein the first blocking group and the second blocking group may be the same or different.

11. The compound according to claim 1, wherein the first blocking groups at one end and at another end of the first linear molecule may be the same or different, and the second blocking groups at one end and at another end of the second linear molecule may be the same or different.

12. The compound according to claim 1, wherein the first and/or the second cyclic molecule are/is selected from the group consisting of cyclodextrins, crown ethers, benzo-crowns, dibenzo-crowns and dicyclohexano-crowns.

13. The compound according to claim 1, wherein the first and/or the second linear molecule are/is selected from the group consisting of polyethylene glycols, polyisoprene, polyisobutylene, polybutadiene, polypropylene glycols, polytetrahydrofuran, polydimethylsiloxane, polyethylene and polypropylene.

14. The compound according to claim 1, wherein the blocking group is selected from the group consisting of dinitrophenyl groups, cyclodextrins, adamantane groups, trityl groups, fluoresceins and pyrenes.

15. The compound according to claim 1, wherein the blocking group is a backbone or a side chain of a macromolecule having a molecular weight of 1,000 to 1,000,000.

16. The compound according to claim 1, wherein at least one of the first cyclic molecules and at least one of the second cyclic molecules are chemically bonded by a crosslinking agent.

17. The compound according to claim 1, wherein the crosslinking agent has a molecular weight of less than 2,000, preferably less than 1,000, more preferably less than 600, and most preferably less than 400.

18. The compound according to claim 16, wherein the crosslinking agent is selected from the group consisting of cyanuric chloride, trimesoyl chloride, terephthaloyl chloride, epichlorohydrin, dibromobenzene, glutaraldehyde, phenylene diisocyanates, tolylene diisocyanates, divinylsulfone, 1,1-carbonyldiimidazole and alkoxysilanes.

19. The compound according to claim 1, wherein the cyclic molecules are alpha-cyclodextrin, the linear molecule is polyethylene glycol, the blocking group is a dinitrophenyl group, and the crosslinking agent is cyanuric chloride.

20. The compound according to claim 1, which is a viscoelastic material or a solvent-absorbing material.

21. Crosslinked polyrotaxane comprising at least two polyrotaxane molecules, each of which has a polyethylene glycol molecule and an alpha-cyclodextrin molecule, the polyethylene glycol molecule having the alpha-cyclodextrin molecule included in a skewered manner which allows the polyethylene glycol molecule to pass through the opening of the alpha-cyclodextrin molecule, and having at each end a blocking group which is placed so as to prevent the elimination of the alpha-cyclodextrin molecule, wherein the crosslinked polyrotaxane is formed by linking the alpha-cyclodextrin molecule of each of the two polyrotaxane molecules to each other via chemical bonding.

22. The crosslinked polyrotaxane according to claim 21, comprising a first blocking group having bulkiness and/or ionic property, thereby preventing the elimination of the first cyclic molecule.

23. The crosslinked polyrotaxane according to claim 21, comprising a second blocking group having bulkiness and/or ionic property, thereby preventing the elimination of the second cyclic molecule.

24. Crosslinked polyrotaxane comprising at least two polyrotaxane molecules, each of which has a polyethylene glycol molecule and an alpha-cyclodextrin molecule, the polyethylene glycol molecule having the alpha-cyclodextrin molecule included in a skewered manner which allows the polyethylene glycol molecule to pass through the opening of the alpha-cyclodextrin molecule, and having at each end a blocking group which is bulky enough to prevent the elimination of the alpha-cyclodextrin molecule, wherein the crosslinked polyrotaxane is formed by linking the alpha-cyclodextrin molecules of each of the two polyrotaxane molecules to each other via chemical bonding.

25. The crosslinked polyrotaxane according to claim 21, wherein each of the two polyrotaxane molecules has at least two alpha-cyclodextrin molecules included in a skewered manner by means of a single polyethylene glycol molecule.

26. The crosslinked polyrotaxane according to claim 21, wherein the polyethylene glycol molecule has the alpha-cyclodextrin molecules included in a skewered manner at an amount of 0.001 to 0.6 of a maximum inclusion amount, which is defined as an amount at which alpha-cyclodextrin molecules can be included at maximum when a polyethylene glycol molecule has plural alpha-cyclodextrin molecules included in a skewered manner, and the amount at maximum is normalized to be 1.

27. The crosslinked polyrotaxane according to claim 21, wherein the blocking group is selected from the group consisting of dinitrophenyl groups, cyclodextrins, adamantane groups, trityl groups, fluoresceins and pyrenes.

28. The crosslinked polyrotaxane according to claim 21, wherein the polyethylene glycol molecule has a molecular weight of not less than 1,000, for example, 1,000 to 1,000,000, preferably not less than 5,000, for example, 5,000 to 1,000,000 or 5,000 to 500,000, and more preferably not less than 10,000, for example, 10,000 to 1,000,000, 10,000 to 500,000, or 10,000 to 300,000.

29. The crosslinked polyrotaxane according to claim 21, wherein the blocking group is a backbone or a side chain of a macromolecule having a molecular weight of 1,000 to 1,000,000.

30. The crosslinked polyrotaxane according to claim 21, wherein the chemical bonding is formed by means of a crosslinking agent.

31. The crosslinked polyrotaxane according to claim 30, wherein the crosslinking agent has a molecular weight of less than 2,000, preferably less than 1,000, more preferably less than 600, and most preferably less than 400.

32. The crosslinked polyrotaxane according to claim 30, wherein the crosslinking agent is selected from the group consisting of cyanuric chloride, trimesoyl chloride, terephthaloyl chloride, epichlorohydrin, dibromobenzene, glutaraldehyde, phenylene diisocyanates, tolylene diisocyanates, divinylsulfone, 1,1-carbonyldiimidazole and alkoxysilanes.

33. The crosslinked polyrotaxane according to claim 21, wherein the crosslinked polyrotaxane is a viscoelastic material or a solvent-absorbing material.

34. A process for producing a compound comprising crosslinked polyrotaxane, comprising the steps of: mixing a cyclic molecule and a linear molecule to prepare polyrotaxane in which the linear molecule has the cyclic molecule included in a skewered manner which allows the linear molecule to pass through the opening of the cyclic molecules, blocking each end of the linear molecule with a blocking group so as to prevent the elimination of the cyclic molecule from the skewered state, and crosslinking two or more polyrotaxanes by linking the cyclic molecules to each other via chemical bonding, and wherein each opening of the cyclic molecules is substantially cyclic.

35. A process for producing a compound comprising crosslinked polyrotaxane, comprising the steps of: mixing a cyclic molecule and a linear molecule to prepare polyrotaxane in which the linear molecule has the cyclic molecule included in a skewered manner which allows the linear molecule to pass through the opening of the cyclic molecule, blocking each end of the linear molecule with a blocking group so as to prevent the elimination of the cyclic molecules from the skewered state, and crosslinking two or more polyrotaxanes by linking the cyclic molecules to each other via chemical bonding.

36. The process according to claim 34, wherein the blocking group at each end of the linear molecule may be the same or different.

37. The process according to claim 34, wherein the blocking group has bulkiness and/or ionic property, so as to prevent the elimination of the cyclic molecules from the skewered state.

38. The process according to claim 34, wherein in the step of preparing polyrotaxane, the preparing conditions including the preparation time and temperature are set and/or controlled, such that at least two cyclic molecules are included in a skewered manner by means of a single linear molecule.

39. The process according to claim 34, wherein in the step of preparing polyrotaxane, the preparing conditions are controlled, such that the linear molecule has the cyclic molecules included in a skewered manner at an amount of 0.001 to 0.6, preferably 0.01 to 0.5, and more preferably 0.05 to 0.4, of a maximally includable amount, which is defined as an amount at which the cyclic molecule can be included at maximum when the linear molecule has the cyclic molecules included in a skewered manner, and the maximally includable amount is normalized to be 1.

40. The process according to claim 34, wherein the compound is a viscoelastic material or a solvent-absorbing material.

41. A process for producing a compound comprising crosslinked polyrotaxane, comprising the steps of: mixing alpha-cyclodextrin and polyethylene glycol to prepare polyrotaxane in which the polyethylene glycol has the alpha-cyclodextrin included in a skewered manner which allows the polyethylene glycol to pass through the opening of the alpha-cyclodextrin, blocking each end of the polyethylene glycol molecule with a blocking group so as to prevent the elimination of the alpha-cyclodextrins from the skewered state, and crosslinking two or more polyrotaxane molecules by linking the alpha-cyclodextrins to each other via chemical bonding.

42. The process according to claim 41, wherein the blocking group has bulkiness and/or ionic property, so as to prevent the elimination of the cyclic molecule from the skewered state.

43. The process according to claim 41, wherein in the step of preparing polyrotaxane, the preparing conditions including the preparation time and temperature are set and/or controlled, such that at least two alpha-cyclodextrin molecules are included in a skewered manner by means of the single polyethylene glycol molecule.

44. The process according to claim 41, wherein in the step of preparing polyrotaxane, the preparing conditions are controlled, such that the polyethylene glycol molecule has the alpha-cyclodextrin included in a skewered manner at an amount of 0.001 to 0.6, preferably 0.01 to 0.5, and more preferably 0.05 to 0.4, of a maximally includable amount, which is defined as an amount at which alpha-cyclodextrin can be included at maximum when the polyethylene glycol molecule has alpha-cyclodextrin included in a skewered manner, and the maximally includable amount is normalized to be 1.

45. The process according to claim 41, wherein the compound is a viscoelastic material or a solvent-absorbing material.

46. A process for producing a compound comprising crosslinked polyrotaxane, comprising the steps of: providing a bicyclic molecule with a first and second substantial rings, mixing the bicyclic molecule with a first linear molecule and a second linear molecule to prepare crosslinked polyrotaxane in which the first linear molecule has the bicyclic molecule included in a skewered manner which allows the first linear molecule to pass through the opening of the first ring of the bicyclic molecule, and the second linear molecule has the bicyclic molecule included in a skewered manner which allows the second linear molecule to pass through the opening of the second ring of the bicyclic molecule, and which is formed by linking the bicyclic molecules; and blocking each end of the linear molecules with a blocking group so as to prevent the elimination of the bicyclic molecules from the skewered state.

47. The process according to claim 46, wherein the first and second linear molecules may be the same or different.

48. The process according to claim 46, wherein the first and/or second substantial ring are/is an open ring, and before and/or after the blocking step, the process comprises the step of closing the open ring.

49. The process according to claim 46, wherein the blocking group at each end of the linear molecule may be the same or different.

50. The process according to claim 46, wherein the blocking group has bulkiness and/or ionic property, so as to prevent the elimination of the cyclic molecules from the skewered state.

51. The process according to claim 46, wherein in the step of preparing crosslinked polyrotaxane, the linear molecule has at least two bicyclic molecules included in a skewered manner.

52. The process according to claim 46, wherein in the step of preparing crosslinked polyrotaxane, the preparing conditions including the preparation time and temperature are set or controlled, such that at least two bicyclic molecules are included per linear molecule in a skewered manner.

53. The process according to claim 46, wherein in the step of preparing crosslinked polyrotaxane, the bicyclic molecule is included in a skewered manner through the linear molecule at an amount of 0.001 to 0.6 of a maximally includable amount, which is defined as an amount at which the bicyclic molecule can be included at maximum, when the linear molecule has the bicyclic molecule included in a skewered manner, and the maximally includable amount is normalized to be 1.

54. The process according to claim 46, wherein in the step of preparing crosslinked polyrotaxane, the preparing conditions including the preparation time and temperature are set or controlled, such that the bicyclic molecule is included in a skewered manner through the linear molecule at an amount of 0.001 to 0.6 of the maximally includable amount, which is defined as an amount at which the bicyclic molecule can be included at maximum, when the linear molecule has the bicyclic molecule included in a skewered manner, and the maximally includable amount is normalized to be 1.

55. The process according to claim 46, wherein the compound is a viscoelastic material or a solvent-absorbing material.

56. A compound comprising crosslinked polyrotaxane formed by crosslinking a first polyrotaxane and a second polyrotaxane, wherein the first polyrotaxane has a first linear molecule and a first cyclic molecule, the first linear molecule having the first cyclic molecule included in a skewered manner which allows the first linear molecule to pass through the opening of the first cyclic molecule, and having at each end a first blocking group which is placed so as to prevent the elimination of the first cyclic molecule, the second polyrotaxane has a second linear molecule and a second cyclic molecule, the second linear molecule having the second cyclic molecule included in a skewered manner which allows the second linear molecule to pass through the opening of the second cyclic molecule, and having at each end a second blocking group which is placed so as to prevent the elimination of the second cyclic molecule, each ring of the first and second cyclic molecules is substantially cyclic, and the crosslinking is formed via chemical bonding between at least one of the first cyclic molecules and at least one of the second cyclic molecules, and wherein the first cyclic molecule is movable between the ends of the first linear molecule, and the second cyclic molecule is movable between the ends of the second linear molecule, so that when force is applied to the compound, the first and second cyclic molecules are moved, so as for the force to be equally dispersed, whereby providing the compound having viscoelastic property.

57. The compound comprising crosslinked polyrotaxane according to claim 1, wherein the first cyclic molecule is movable between the ends of the first linear molecule, the second cyclic molecule is movable between the ends of the second linear molecule, so that when force is applied to the compound, the first cyclic and second cyclic molecules are moved, so as for the force to be equally dispersed, whereby providing the compound having viscoelastic property.

58. A compound comprising crosslinked polyrotaxane formed by crosslinking a first polyrotaxane and a second polyrotaxane, wherein the first polyrotaxane has a first linear molecule and a first cyclic molecule, the first linear molecule having the first cyclic molecule included in a skewered manner which allows the first linear molecule to pass through the opening of the first cyclic molecule, and having at each end a first blocking group which is placed so as to prevent the elimination of the first cyclic molecule, the second polyrotaxane has a second linear molecule and a second cyclic molecule, the second linear molecule having the second cyclic molecule included in a skewered manner which allows the second linear molecule to pass through the opening of the second cyclic molecule, and having at each end a second blocking group which is placed so as to prevent the elimination of the second cyclic molecule, each ring of the first and second cyclic molecules is, and the crosslinking is formed via chemical bonding between at least one of the first cyclic molecules and at least one of the second cyclic molecules, and wherein the viscoelastic property of the compound is controlled by controlling any one selected from the group consisting of: an amount of the first cyclic molecule to be included through the first linear molecule; an amount of the second cyclic molecule to be included through the second linear molecule; molecular weight and rigidity of the first and second linear molecules; and degrees of crosslinking between the first cyclic molecule and the second cyclic molecule.

59. The compound according to claim 1, wherein the viscoelastic property of the compound is controlled by controlling any one selected from the group consisting of: an amount of the first cyclic molecule to be included through the first linear molecule; an amount of the second cyclic molecule to be included through the second linear molecule; molecular weight and rigidity of the first and second linear molecules; and degrees of crosslinking between the first cyclic molecule and the second cyclic molecule.

60. A contact lens comprising the compound according to claim 1.

61. A biomaterial comprising the compound according to claim 1.

62. A medical material comprising the compound according to claim 1.

63. A tire comprising the compound according to claim 1.

64. A coating material comprising the compound according to claim 1.

65. An adhesive comprising the compound according to claim 1.

66. The crosslinked polyrotaxane according to claim 21, wherein the alpha-cyclodextrin molecules are movable between ends of the polyethylene glycol molecule, and when force is applied to the crosslinked polyrotaxane, the alpha-cyclodextrin molecules are moved relatively to the polyethylene glycol molecule, so that the force can be equally dispersed, whereby providing the crosslinked polyrotaxane having viscoelastic property.

67. The crosslinked polyrotaxane according to claim 21, wherein the viscoelastic property of the crosslinked polyrotaxane is controlled by controlling any one selected from the group consisting of: an amount of the alpha-cyclodextrin molecule to be included through the polyethylene glycol molecule; molecular weight and rigidity of the polyethylene glycol; and degrees of crosslinking between the alpha-cyclodextrins.

68. A contact lens comprising the crosslinked polyrotaxane according to claim 21.

69. A biomaterial comprising the crosslinked polyrotaxane according to claim 21.

70. A medical material comprising the crosslinked polyrotaxane according to claim 21.

71. A tire comprising the crosslinked polyrotaxane according to claim 21.

72. A coating material comprising the crosslinked polyrotaxane according to claim 21.

73. An adhesive comprising the crosslinked polyrotaxane according to claim 21.

* * * * *